(12) United States Patent
Breitschwerdt et al.

(10) Patent No.: US 7,115,385 B2
(45) Date of Patent: Oct. 3, 2006

(54) MEDIA AND METHODS FOR CULTIVATION OF MICROORGANISMS

(75) Inventors: Edward B. Breitschwerdt, Fuquay-Varina, NC (US); Sushama Sontakke, Gloucester (CA)

(73) Assignee: North Carolina State University, Raleigh, NC (US)

( * ) Notice: Subject to any disclaimer, the term of this patent is extended or adjusted under 35 U.S.C. 154(b) by 395 days.

(21) Appl. No.: 10/208,352

(22) Filed: Jul. 30, 2002

(65) Prior Publication Data

US 2003/0148499 A1 Aug. 7, 2003

Related U.S. Application Data

(60) Provisional application No. 60/309,688, filed on Aug. 2, 2001.

(51) Int. Cl.
| | |
|---|---|
| *A61K 49/00* | (2006.01) |
| *C12N 1/00* | (2006.01) |
| *C12N 1/12* | (2006.01) |
| *C12N 1/20* | (2006.01) |
| *C12Q 1/02* | (2006.01) |

(52) U.S. Cl. .................. 435/29; 424/9.1; 435/243; 435/252.1

(58) Field of Classification Search .......... 435/243
See application file for complete search history.

(56) References Cited

U.S. PATENT DOCUMENTS

| | | | | |
|---|---|---|---|---|
| 3,816,260 A | * | 6/1974 | Sugiyama | 435/206 |
| 4,217,411 A | | 8/1980 | Le Frock et al. | |
| 5,034,331 A | * | 7/1991 | Brewer | 435/305.4 |
| 5,070,014 A | | 12/1991 | Dorn | |
| 5,254,533 A | * | 10/1993 | Kiener et al. | 514/8 |
| 5,424,202 A | * | 6/1995 | Ingram et al. | 435/161 |
| 5,677,127 A | | 10/1997 | Hogan et al. | |
| 6,551,591 B1 | * | 4/2003 | Lee | 424/115 |
| 6,562,958 B1 | * | 5/2003 | Breton et al. | 536/23.7 |

FOREIGN PATENT DOCUMENTS

EP  0 460 414 A2  12/1991

OTHER PUBLICATIONS

International Search Report, PCT/US02/24329 Jun. 18, 2003.

* cited by examiner

*Primary Examiner*—David M. Naff
*Assistant Examiner*—Deborah K. Ware
(74) *Attorney, Agent, or Firm*—Myers Bigel Sibley & Sajovec, P.A.

(57) ABSTRACT

The present invention provides culture media and methods for culturing organisms, preferably microorganisms, more preferably fastidious microorganisms. Also provided are methods of isolating and detecting organisms using the inventive culture media.

47 Claims, No Drawings

MEDIA AND METHODS FOR CULTIVATION OF MICROORGANISMS

RELATED APPLICATION INFORMATION

This application claims the benefit of U.S. Provisional Application No. 60/309,688, filed Aug. 2, 2001, the disclosure of which is incorporated by reference herein in its entirety.

FIELD OF THE INVENTION

The present invention relates to novel culture media for growing and isolating microorganisms, in particular bacteria, as well as methods of growing and isolating the microorganisms using the novel growth media.

BACKGROUND OF THE INVENTION

Traditional approaches for isolating pathogenic agents have been unsuccessful in a substantial number of disease conditions where an infectious etiology is suspected, e.g., Crohn's disease, ulcerative colitis, Wegener's granulomatosis, rheumatoid arthritis, tropical sprue, systemic lupus erythrematosus, Kawasaki's disease, and other chronic diseases (Costeron et al., (1999) *Science* 284:1318; Relman, (1999) *Science* 284:1308). Use of broad range PCR or other molecular approaches (e.g., microarrays) have been suggested to identify the causative agent underlying infectious disease states (Fredricks et al., (1999) *Clin. Infect. Dis.* 29:475; Relman, (1999) *Science* 284:1308; Cummings et al., (2000) *Emerg. Infect. Dis.* 6:513; Diehn et al., (2001) *Curr. Opin. Microbiol* 4:95). However, these approaches do not result in isolation of the organism for use in further studies and are cumbersome for many experimental applications (e.g., antimicrobial and disease studies and/or vaccine development).

Microorganisms may be introduced into mammalian subjects by a variety of mechanisms, including inhalation, ingestion, severe or persistent insect bites, injections, prolonged use of saline needles, implantation of medical devices, or exposure during surgical techniques. The introduced organisms may have an affinity for red blood cells (RBCs) or nerve cells and may even grow in these cells. Infections may be particularly severe in the case of immunocompromised patients, such as those on immunosuppressive drugs, infected with HIV, or having particular genetic conditions. In addition, certain patients, such as those with diabetes or cystic fibrosis, are particularly susceptible to infection (Ahkee et al., (1995) *J. Ky. Med. Assoc.* 93:511; Costeron, (2001) *Trends Microbiol* 9:50; Costeron et al., (1999) *Science* 284:1318). For example, it is known that cystic fibrosis patients, who suffer a defect in the chloride transport system, are susceptible to infection with *Ps. aeruginosa*, as well as other microorganisms. In these patients, antibodies to alkaline phosphatase, exotoxin A, and elastase of *Ps. aeruginosa* have been detected (Costeron, (2001) *Trends Microbiol* 9:50; Costeron et al., (1999) *Science* 284:1318).

Various gram-negative urinary tract or local skin flora may gain entrance into the body, e.g., due to insect bites, wounds, injuries and the like, causing infection in synovial fluids and joint inflammation. Moreover, *Streptococcus* spp. and *Staphylococcus* spp. are frequently linked to disease (Costeron et al., (1995) *Annu. Rev. Microbiol.* 49:711). Infections by some agents are facilitated by insect transmission, for example, *Bartonella* spp. infections transmitted by fleas, lice or ticks are introduced into cats, dogs, humans and other mammals (see, e.g., Shaw et al., (2001) *Trends Parasitol.* 17:74; Munana et al. (2001) *Infect. Immun.* 69:564; Breitschwerdt et al., (2000) *Clin. Microbiol Rev.* 13:428).

Microorganisms may cause pathology in multiple organs or tissues in the host, not because of direct invasion or growth in the affected tissues, but rather as a result of molecular mimicry between self-antigens and microbial cell antigens, which induces immune-mediated tissue destruction. Molecular mimicry between bacterial or viral proteins and endogenous molecules has been implicated in various autoimmune diseases, including insulin dependent diabetes mellitus, Gillian Barre syndrome, multiple sclerosis and autoimmune herpes stromal keratitis (Relman, *Science* 284: 1308). After initiation of the disease, epitope spreading leads to the maintenance and progression of inflammation.

*Bartonella* are vector-transmitted, blood-borne, intracellular gram-negative bacteria that can induce prolonged infection in the host. Persistent infections in domestic and wild animals result in a reservoir of *Bartonella* in nature that can serve as a source for human infection. The prevalence can range from 50–95% in selected rodent, cat, deer or cattle populations. Considering the extensive animal reservoirs and the large number of insects that have been implicated in the transmission of *Bartonella* spp., both animal and human exposure to these organisms may be more substantial than is currently realized.

Recent observations support a role for *Bartonella* as animal as well as human pathogens. Dogs infected with *Bartonella* spp. can develop lameness, endocarditis, granulomatous lymphadenitis and peliosis hepatis, lesions that are also reported in association with human infection. In felines, recent reports describe a correlation between *Bartonella* seroreactivity and renal disease, stomatitis, or lymphadenopathy.

The spectrum of diseases attributable to *Bartonella* spp. now includes lymphadenopathy (i.e., cat scratch disease or CSD), bacillary angiomatosis, bacillary peliosis, bacteremia, endocarditis, myositis, retinitis, endocarditis, bacillary angiomatosis, osteolysis, polyarthritis, leukoclastic vasculitis, fever of unknown origin (Trench Fever) and hemolytic anemia (South American bartonellosis). *Bartonella bacilliformis, B. quintana, B. elizabethae, B. vinsonii* subspecies *arupensis., B. clarridgeiae* and *B. henselae* have been associated with these disease manifestations in human patients (Anderson et al., (1997) *Clin. Microbiol. Rev.* 10:203).

In addition, a new α-2 proteobacterium, provisionally designated Rasbo bacterium, has been isolated from a human patient with evidence of myocardial disease. *B. quinitana,* which is transmitted by the human body louse, is the infectious agent underlying epidemics of trench fever during World War I. There also appears to be a correlation between Bartonellosis and renal disease in human patients.

Recently, a novel *Bartonella* subspecies, designated as *B. vinsonii* subspecies *berkhoffi* (ATTC strain 51672) has been identified. In one study, cardiac arrhythmias, endocarditis, or myocarditis was observed in 12 dogs, 11 of which were seroreactive to *B. vinsonii* subsp. *berkhoffi* antigens. It appears that *B vinsonii* subsp. *berkhoffi* and closely-related species of alpha-proteobacteria may be an important, previously unrecognized, cause of arrhythmias, endocarditis, myocarditis, syncope, and sudden death in dogs.

There is also increasing evidence that several *Bartonella* spp., including *B. quintana, B. elizabethae, B. vinsonii* and *B. henselae* are responsible for cases of culture-negative endocarditis in human patients. A retrospective study from France identified patients with bartonella endocarditis that had not previously been diagnosed using conventional microbiologic techniques. To date, bartonella endomyocarditis in dogs has only been associated with *B. vinsonii* (*berkhoffii*); however, the inventors' laboratory has obtained molecular evidence of *B. henselae* infection in a dog with peliosis hepatis (Kitchell et al., (2000) *J. Am. Vet Med. Assoc.* 216:519), a liver lesion that has recently been associated with either *B. henselae* or *B. quintana* infection in human patients. Not only does this observation provide the first microbiologic or molecular evidence for persistent *B. henselae* infection in dogs, it also indicates that *B. henselae* might be implicated in future studies of culture-negative endocarditis in dogs.

In human patients, bartonella endocarditis has been reported in children and in adults, particularly homeless individuals with exposure to *B. quintana* as a result of louse infestation. *Bartonella* endocarditis has also been reported in association with immune-complex glomerulonephritis. Recently, it has been reported that infection due to *Bartonella weisii* species in North Carolina beef cattle (Breitschwerdt et al., (2001) *J. Clin. Microbiol* 39:879).

Further, *Chlamydia trachomatis*, *Ch. psittaci*, and *Ch. pneumoniae* have been linked to heart disease. Infection with *Ch. trachomatis* has been reported to result in the production of auto-antibodies to heart muscle specific epitopes. Other *Chlamydia* spp. bear epitopes that are similar to heart proteins (Bachmaier et al., (1999) *Science* 283:1335). Similarly, in patients with multiple sclerosis, antibodies to *C. pneumoniae* are routinely detected, but this microorganism has not yet been isolated from these patients. Further, in patients with Crohn's disease or ankylosing spondylitis, *Klebsiella pneumoniae* antibodies are directed against collagen types I, III, IV and V.

Accordingly, there is a need in the art for improved media for culturing and isolating microorganisms. Moreover, there is a need in the art for improved methods of culturing, detecting and identifying these, and other, microorganisms that are associated with animal and human disease.

SUMMARY OF THE INVENTION

The present inventors have made the discovery that under particular culture conditions, fastidious microorganisms may be successfully cultured and isolated, even microorganisms for which no detectable growth may be achieved by conventional microbiological culturing techniques (e.g., blood agar, chocolate agar, bile salt agar, Eagle's medium, Dulbecco's modified Eagle's medium, F12 medium, and the like). Indeed, the present inventors have cultured microorganisms from samples (e.g., cerebrospinal fluid) that would appear to be sterile by conventional techniques.

Moreover, the methods and culture media of the present invention have been used to culture microorganisms of clinical significance for which there have heretofore been no reports of successful culture or isolation (e.g., a new species *Corynebacteria*). *Corynebacteria* other than *C. diphtheriae* and *C. sepedonicum* have previously been identified by PCR amplification and sequencing of the 16S rRNA, but the inventors are not aware of any reports of these newly-identified pathogens being successfully cultured or isolated.

Further, the methods and culture media of the invention may be used to culture, isolate, detect and/or isolate microorganisms that are the etiologic agents of disease.

The present investigations suggest that microorganisms such as the Proteobacteria, in particular *Bartonella* and nanobacteria, are far more prevalent in animal populations than previously recognized.

Conventional methods of culturing microorganisms from mammalian sources have often employed conditions that emulate mammalian biology. Typical media for culturing mammalian cells include sheep's blood agar, chocolate agar, bile salt agar, Dulbecco's modified Eagle's medium, Eagle's medium, and F12 medium. While not wishing to be held to any particular theory of the invention, it appears that many fastidious organisms are not well-adapted to these culture conditions. For example, they may require that biosynthetic building blocks or other organic molecules (e.g., lipids, sugars, nucleotides, vitamins, minerals and/or amino acids) be supplied in the medium for which they lack adequate synthetic capacity. To illustrate, the microbe may require particular lipids as building blocks for cell walls and/or cell membranes, all of the ribonucleotides and deoxynucleotides as building blocks for RNA and DNA molecules, all vitamins required for the production and functioning of enzymes for energy generation and utilization, as well as appropriate carbon and nitrogen sources. Likewise, some microorganisms may require that amino acids be supplied in the form of protein hydrolysates or free amino acids. It further appears that insect-borne and arachnid-borne pathogens may be cultured more efficiently under culturing conditions typically used for insect cells as compared with mammalian cells.

Thus, there is a need for improved techniques used for the cultivation of microorganisms from clinical samples' It is possible that in the animal host, introduced microbes may (1) have metabolic diversity as judged by the ability to cause disease at different tissue sites in the body, (2) find the conditions in the host to be sub-optimal or unfavorable for their growth as judged by very slow development of disease, (3) have impaired metabolism, and/or (4) have adapted to grow in the given animal host. By providing conditions and nutrients similar to the universal minimum requirements for the growth of any type of free living chemoorganotrophic microbial cell, it may be possible to grow a variety of organisms found in clinical samples in the media of the present invention. Alternatively, by providing lipids, sugars, amino acids, vitamins, and the like, that closely simulate the conditions within the animal host tissue(s) where symptoms are predominant, it is possible to grow causative agents underlying disease. Traditional mammalian tissue culture media do not contain many carbon and nitrogen substrates that are found in the mammalian host. In contrast, insect tissue culture media do contain a variety of lipids, sugars and/or organic acids and more closely simulate conditions within mammalian hosts.

In this manner, the infectious agents underlying numerous disease states can be more readily identified. For example, a microorganism that is cultured and isolated from a clinical sample using the inventive culture media can be used as an antigen to determine whether the patient has developed antibodies thereto, thereby implicating the microbe as a likely causative agent of disease in the patient.

The present invention finds use in methods of: (1) cultivating and growing microorganisms from clinical samples derived from animals or humans; (2) growing and isolating fastidious (e.g., cell wall deficient, immunologically impaired, and/or stressed) microorganisms, which may not be cultured with currently available media; (3) growing, identifying, isolating and/or detecting microorganisms associated with disease; and (4) culturing microorganisms for vaccine production, antigen production, or production of metabolites (e.g., in fermentors or small reactors, including shaker flasks).

Accordingly, in particular embodiments, the present invention provides a culture medium for growing a fastidious microorganism comprising sufficient biosynthetic building blocks and other organic molecules to support the growth of the fastidious microorganism in culture.

As a further aspect, the present invention provides a method of culturing a fastidious microorganism comprising culturing a sample containing a fastidious microorganism in a culture medium comprising sufficient biosynthetic building blocks and other organic molecules to support the growth of a fastidious microorganism in culture for a time and under conditions sufficient to grow a fastidious microorganism present in the sample.

As still a further aspect, the present invention provides a method of detecting a fastidious microorganism in a sample comprising: culturing a sample containing a fastidious microorganism in a culture medium comprising sufficient biosynthetic building blocks and other organic molecules to support the growth of a fastidious microorganism in culture for a time and under conditions sufficient to grow the fastidious microorganism; and detecting the fastidious microorganism.

As another aspect, the present invention provides a method of identifying a fastidious microorganism in a sample, comprising: culturing a sample containing a fastidious microorganism in a culture medium comprising sufficient biosynthetic building blocks and other organic molecules to support the growth of a fastidious microorganism in culture for a time and under conditions sufficient to grow the fastidious microorganism; and identifying the fastidious microorganism.

As a further aspect, the present invention provides a method of identifying a compound that binds to a fastidious microorganism, comprising: culturing a sample containing a fastidious microorganism in a culture medium comprising sufficient biosynthetic building blocks to support the growth of a fastidious microorganism in culture for a time and under conditions sufficient to grow the fastidious microorganism; contacting the fastidious microorganism with a compound; and detecting binding between the fastidious microorganism and the compound.

As yet a further aspect, the present invention provides a method of diagnosing a mammalian subject with an infection by a fastidious microorganism, comprising: culturing a sample from a mammalian subject containing a fastidious microorganism in a culture medium comprising sufficient biosynthetic building blocks and other organic molecules to support the growth of a fastidious microorganism in culture for a time and under conditions sufficient to grow the fastidious microorganism; identifying the fastidious microorganism in the cultured sample; diagnosing the subject as having an infection with the fastidious microorganism. Also provided are methods of diagnosing disorders associated with infection by particular pathogenic organisms.

These and other aspects of the invention and set forth in more detail in the description of the invention below.

DETAILED DESCRIPTION OF THE INVENTION

As used herein, a "culture medium" has its understood meaning in the art, and may be a cell, tissue or organ culture medium. The culture medium may be used to maintain, grow and/or isolate organisms. The culture medium can be a liquid, semi-solid, or solid culture medium. The culture media of the invention may be used to grow any suitable organism, including bacteria, yeast, protozoa, and fungi. Preferably, the medium is used to culture bacteria. The medium may also be used to alter the metabolic state of the organism, e.g., to convert a microbial cell from a spore or nonculturable state to a vegetative and culturable state.

The term "microorganism" as used herein has its conventional meaning in the art and includes bacteria, protozoa, yeasts, molds, and viruses. In preferred embodiments, the microorganism is a bacterium, more preferably, a *Proteobacterium* (including subgroups, alpha, beta, delta and gamma), still more preferably the bacterium is a member of the alpha-*Proteobacteria* (e.g., *Bartonella, Brucella, Rasbo bacteria, Afipa*, and the like), including nanobacteria. In particular preferred embodiments, the microorganism is a *Bartonella* including but not limited to *B. vinsonii* (e.g., subsp. *berkhoffi*), *B. henselae, B. weissi, B. clarridgeiae, B. quintana*, and *B. elizabethae*. Alternatively, in other preferred embodiments, the microorganism is *Burkholdrea pickettii, Streptococcus thermophillis*, a *Corynebacterium*, a bacterium belong to the group Firmicutes, Fusobacteria, Planctomycetales, Spirochete, or division *Arachea bacteria*.

In particular preferred embodiments, the microorganism is a nanobacterium. Nanobacteria are reported to be small, slow-growing, mineral-forming bacteria. Nanobacteria have been characterized as spherical with diameters of about 50–500 nanometers, and will pass through a 0.2 :m filter. A particular species of nanobacteria, designated *Nanobacterium sanguineum*, has previously been described in U.S. Pat. No. 5,135,851 and by Kajander et al., (1998) *Proc. Nat. Acad. Sci. USA* 95:8274.

As used herein, a "fastidious" organism (including a fastidious microorganism) is an organism that is recalcitrant to culturing using conventional media (e.g., sheep's blood agar, chocolate agar, bile salt agar, Dulbecco's modified Eagle's medium, Eagle's medium, F12 medium, and the like), and will typically have more stringent requirements with respect to the chemical composition of the media. For example, the organism may require that particular organic molecules be provided in the medium due to defective or insufficient enzymatic machinery for synthesis of nutrients such as vitamins, amino acids, lipids, cofactors such as NAD, NADH, nucleosides or free radical scavengers. Alternatively, or additionally, the fastidious organism may have a requirement that particular organic molecules be supplied in the medium or, conversely, have an intolerance for certain components (e.g., sugars) used in many media.

The fastidious organism may be a defective or injured organism due to injury or stress upon introduction into the host, e.g., as a result of anti-bacterial mechanisms by the host, antibiotics or surfactant production by the lung (these microorganisms may be also be designated as "immunologically impaired"). For example, the organism may lack a cell wall, alternatively, the cell wall of the organism may be damaged or even destroyed. Likewise, there may be a defect in cell wall synthesis by the organism. In addition, transport mechanisms or cellular metabolic pathways may be disrupted as a result of injury or stress to the organism. Alternatively, the fastidious organism may form a viable, but non-culturable microbe, which is a metabolically inactive form of the organism. Defective organisms that have suffered stress, or metabolically-inactive microbes, are more resistant or refractory to standard culturing and isolation techniques. As a further alternative, the fastidious organism may have adapted to the host environment, and may not be able to tolerate culture conditions that deviate substantially from conditions within the host.

It has been estimated that 99% of microorganisms from environmental sources are in a viable but nonculturable state (Costeron et al., (1999) *Science* 284:1318; Costeron et al., (1995) *Annu. Rev. Microbiol* 49:711). While not wishing to be held to any particular theory, it is possible that culture improvements or quorum signals may need to be supplied to bring these "inert" microbial cells back to a reproductive state that allows them to reproduce in culture by producing planktonic cells (i.e., a "wandering" stage microbial cell, which is culturable) or cells of the biofilm type. In addition to supplying nutrients, the inventive culture media may provide these quorum signals. For example, in particular embodiments, the culture media of the invention contain known quorum signaling chemicals, such as acyl homoserine lactone (Bollinger et al., (2001) *J. Bacteriol* 183:1990; Xie et al., (2000) *J. Bacteriol.* 182:7067). A "quorum signal" is the result of gene expression when a particular cell density is reached. For example, bacteria sense the concentration of the quorum signaling chemical, acyl-homoserine lactone, and when a threshold level is detected, gene expression is triggered which results in expression of enzymes that facilitate culturing of the bacterial cells. As known in the art, acyl homoserine lactones have varying chain lengths; C10 to C12 length acyl group lactones are preferred. If particular species use acyl homoserine lactones of different chain lengths, then these may also be included in the inventive media.

Microorganisms according to the present invention are typically mammalian and/or avian pathogens, more preferably mammalian pathogens. Alternatively, the microorganism may be a reptilian, piscine, amphibian, insect and/or plant pathogen. Preferred microorganisms are insect-borne or arachnid-borne pathogens. The term "pathogen", as used herein, refers to microorganisms that are of clinical relevance because they are believed to be associated with, correlated with, and/or indicative of a disease state or disorder. As used herein, a pathogen is "associated" with a disease state or disorder if it is believed to be a contributing or underlying factor in the development of a disease state or disorder, or it may be more prevalent in individuals with a particular disease or disorder (e.g., Bartonellosis in patients infected with the Human Immunodeficiency Virus).

In particular embodiments, the pathogen is associated with chronic fatigue syndrome, cancer, hypertension, heart disease (e.g., endocarditis), feline urologic disease, hyperadrenalcorticism, mastitis, polyarthritis, immune-mediated hemolytic anemia, thrombocytopenia, cystic fibrosis, cat scratch disease, renal disease, liver disease, prostate disease, or central nervous system disorders.

Alternatively, the microorganism is found in a sample taken from a mammalian or avian source, but is not necessarily a pathogen. The terms "mammalian source" or "mammalian sample" indicate that the sample has been derived from a mammal or a mammalian tissue, organ, cell culture, body fluid or waste product. Likewise, the terms "avian source" or "avian sample" indicate that the sample has been derived from an avian or an avian tissue, organ, cell culture, body fluid or waste product. In particular embodiments, the sample is a body fluid sample (including tissue fluids), a tissue sample, or an organ sample. Exemplary body fluid samples according to the invention include but are not limited to blood, plasma, serum, milk, urine, cerebrospinal fluid (CSF), pleural fluid, pulmonary mucus, sputum, transudates, modified transudates, exudates, chest fluid, abdominal fluid, synovial fluid, peritoneal fluid, lymph, and effusions. Tissue or organ samples (e.g., biopsies or swabs) may be from any tissue or organ in the body and include but are not limited to: skin, liver, heart, kidney, brain and other tissues of the central nervous system, ear, nasal tissue, airway passages, lungs, prostate, ovary, testis, uterus, pancreas, spleen, stomach, esophagus, mouth, intestines, colon, rectum, eye, ear, vagina, cervix, urinary tract, and muscle. In other embodiments, the sample is from a waste product such as a fecal or mucus sample. In still other embodiments, the sample is from an animal product such as meat, eggs, milk or feathers.

The sample may also be derived from an insect or arachnid that is a vector for the microorganism.

Mammals according to the present invention include but are not limited to canine, felines, bovines, caprines, equines, ovines, porcines, rodents, lagomorphs, primates, and the like, and encompass mammals in utero. Canines, felines, bovines, equines and humans are preferred.

Illustrative avians according to the present invention include chickens, ducks, turkeys, geese, quail, pheasant, ratites (e.g., ostrich) and domesticated birds (e.g., parrots and canaries), and include birds in ovo. Chickens and turkeys are preferred.

Other preferred hosts include reptilians (e.g., crocodiles, snakes, turtles), pisces (e.g., fish in commercial hatcheries) and amphibians (e.g., frogs).

Methods of culturing microorganisms from different hosts are known in the art. For example, microorganisms from mammalian samples are typically incubated at around 37° C. In contrast, isolates to be obtained from birds will generally be incubated at both 37° C. and 42° C. (i.e., because some microorganisms with a growth optimum closer to 37° C. may grow in avian hosts, albeit at a reduced rate, and other microbes will have an optimum temperature requirement around 42° C.). Microbes isolated from reptilians and amphibians will typically be incubated at room temperature. Isolates from fish may be incubated at room temperature or at temperatures similar to the water where the piscine host is found. Typically, incubations are carried out under conditions of 90–95% $O_2$/5–10% $CO_2$. Under some circumstances, anaerobic conditions may be used (e.g., 95% $CO_2$), depending upon the host and type of tissue damage at the site from which the clinical sample is derived.

In particular preferred embodiments, the microorganism is an insect-borne or arachnid-borne microorganism, e.g., it is carried and transmitted by insects or arachnids to avian and/or mammalian hosts. Exemplary is *Bartonella quintana* which is transmitted by the human body louse to humans and is associated with trench fever and endocarditis. Exemplary insect-borne or arachnid-borne microorganisms include the *Proteobacteria*, as described hereinabove. Insects and arachnids according to the present invention include but are not limited to spiders, mites, cockroaches, thrips, beetles, ants, endoparasites, fleas, lice, ticks, flies, mosquitoes, bees, wasps, gnats, and other insects which come in contact with avians and/or mammals.

Microorganisms that can be cultured using the inventive culture media include microorganisms that are ubiquitous and grow in the environment, such as in water, on disinfectants, or in soil. Microorganisms that reside in RBCs, nerve cells, macrophages (including microglial cells), and/or form a biofilm in the animal host (e.g., on the inner surfaces of the vagina, blood vessels, lung, cardiac valve, bone, nerve cells, or on outer surfaces of the teeth) may be grown in the media of the invention. Other microorganisms that may be cultured according to the present invention live within a glycocalyx in the animal host (e.g., as noted for *Bartonella* infection of heart, or endocarditis as resulting from infection with *Pasturella hemolytica*).

Exemplary microorganisms that are ubiquitous, can form biofilms, and are linked to human infection are summarized in Table A (taken from Costeron et al., (1999) *Science* 284:1318).

TABLE A

Human Infections involving Ubiquitous Organisms that Produce Biofilms

| Infection or Disease | Common biofilm bacterial spp. |
| --- | --- |
| Dental film | acidogenic gram positive cocci (Streptococci) |
| Otitis media | Non-typeable strains of *H. influenzae* |
| Musculoskeletal | Gram positive cocci (*Staphylococcus* spp.) |
| Biliary tract infection | Enteric bacteria |
| Osteomyelitis | Various bacterial and fungal spp. |
| Native valve endocarditis | Viridans group streptococci |

Cells living in biofilms may form planktonic cells; when under stress, these planktonic microbial cells may be released from the local sites of colonization into the systemic circulation and be found in body fluids such as blood, CSF or urine. These planktonic cells may be cultured from body fluid samples using the inventive media and methods. Because in particular embodiments the composition of the inventive culture media is similar to the composition of body fluids, the media may be used for isolation of planktonic microbial cells.

It is unclear whether cells within the biofilm are truly inert or, alternatively, whether they are in a different metabolic state that is difficult to simulate in the laboratory (sometimes referred to as viable but not culturable cells; Signoretto et al., (2000) *Appl. Environ. Microbiol.* 66:1953; Cappelier et al., (1999) *Appl. Environ. Microbiol.* 65:5154; Alexander et al., (1999) *Appl. Environ. Microbiol* 65:3754; Tholozan et al., (1999) *Appl. Environ. Microbiol.* 65:1110; Costeron et al., (1999) *Science* 284:1318; Costeron et al., (1995) *Annu. Rev. Microbiol.* 49:711). Biofilm cells may grow in size and in number at a very slow rate in patients with chronic diseases. How the biofilm microbes survive and reproduce in nature is not known.

The inventive culture media disclosed may be employed to culture any suitable microorganism. The inventive media may be advantageously employed to culture fastidious organisms by providing an environment that accommodates the more stringent requirements of these organisms. In preferred embodiments, a culture medium of the invention contains all of the amino acids and vitamins essential for growth of the microorganism (e.g., glutamine and/or lysine). The culture medium may also contain protein hydrolysates (e.g., yeast extracts). Alternatively, it is preferred that the medium be a protein-free medium. It is further preferred that the culture medium contain an adequate source of organic acids (e.g., succinic acid, malic acid, and the like) to provide a carbon source for fastidious organisms. Finally, in particular preferred embodiments, the culture medium has a pH below about 7, more preferably below about 6.8 or 6.5. It is also preferred, that the culture medium be maintained at a pH above about 5, more preferably above about 5.5, still more preferably, above about 6. Exemplary culture media have pH in the range of about 6 to about 6.8, or about 6.1 to about 6.5.

Examples of components that are typically lacking or present in insufficient quantities in conventional media include tocopherol (e.g., vitamin $K_1$), β-NAD, β-NADPH, lipid components, nucleotides (including ribosides), coenzyme A, cocarboxylase, citric acid, isocitric acid, malic acid, fumaric acid, succinic acid, tricarboxylic acid cycle (TCA) acids, amino acids that can enter into the TCA cycle after deamination, pyruvic acid, and sugars found in the animal host (such as N-acetyl-glucosamine, which is also required for bacterial cell wall synthesis), glycerol and hemin. For example, as far as the present inventors are aware, no currently available commercial media include citric acid or contain other TCA acids at the levels provided in particular embodiments of the present invention. Other media components that may be required for growth by fastidious organisms include cobalt and ammonium molybdate.

Protein containing media are historically used (most conventional media contain protein hydrolysates and, therefore, the amount of protein depends upon the extent of the hydrolysis) for isolating microbes from clinical samples. In many cases, these protein containing media have failed to isolate microorganisms from clinical samples obtained from patients having conditions such as hypertension, urologic disease, chylothorax, pleural effusion, abdominal transudates, inflammatory CSF, and synovial fluids. In the animal host, low protein conditions exist within urine, CSF and within pleural or peritoneal effusions. Thus, some infectious microorganisms may be recalcitrant to growth in culture in the presence of protein concentrations that are typically used in currently available culture media. The concentration of proteins in the inventive media may be varied (and even completely omitted) to facilitate the growth of microorganisms that are adapted to a low protein or protein-free environment.

The inventive media preferably include reducing agents and anti-oxidants, which simulate conditions in the animal host.

In particular embodiment, the inventive media contain a lipid composition that simulates conditions within the animal host and/or the cell wall composition of the microorganism. In particular preferred embodiments, the culture medium contains lipid components typically found in the brain, e.g., phosphatidyl serine, phosphatidyl inositol, cerobramide, phophoglycolic acid, phosphatidyl ethanolamine, different fatty acid components of phosphatidyl choline, cerebrosides (including different chain lengths), and glycosylated cerebrosides.

In addition, the required components are preferably supplied in the inventive media in sufficiently high concentrations so as to allow growth of microbial cells. The stressed cells can grow in the presence of sufficient concentrations of essential components, even though they may have developed defective transport mechanisms or defective metabolic functions. These defective metabolic functions, as explained earlier, may include defects in the synthesis of TCA cycle enzymes or the synthesis of amino acids, or the synthesis of cell wall enzymes (cell wall alterations have been noted by electron microscopy in *S. aureus* and *S. epidermis* in rabbit tibia models; the cells were large and the partition mechanism was impaired. Further, in the case of *Nocardia* spp. and *Streptococcus* spp. infections, where cell wall deficient forms have been demonstrated in host animals following isolation convert to cells with cell walls; Domingue et al., (1998) *Clin. Microbiol. Rev.* 11:604; Domingue et al., (1997) *Clin. Microbiol. Rev.* 10:320; Domingue et al., (1995) *J. Urol.* 153:1321; Domingue et al., (1993) *J. Urol.* 150:483). These fastidious and surviving microbes may have become dependent on the metabolites supplied by the animal host or supplied by the other microbial agents present in the animal host tissues or body fluids.

Therefore, some fastidious microbes that cause infection in animals may not have sufficient activity of particular enzymes to support growth in vitro. It is likely that this phenotypic plasticity and/or genetic plasticity may be attributable to selection of microbial cells that can survive in the animal host under stress conditions, such as specific nutrient limitation (iron) or in the presence of antimicrobial factors.

One aspect of the present invention is a method of culturing a microorganism (e.g., a mammalian pathogen) comprising culturing the sample comprising the microorganism in a culture medium according to the invention for a time and under conditions sufficient for the organism to grow and, optionally and preferably, be detected or even isolated.

In preferred embodiments, the inventive methods and media may be used to culture fastidious organisms that are recalcitrant to culturing using conventional microbiological techniques, e.g., using conventional mammalian culture media such as blood agar cultures, chocolate agar cultures, bile salt cultures, DMEM, F12 medium, and the like. The microorganism may grow more efficiently with the inventive media and methods than with conventional mammalian culture media. In this way, the present invention may permit greater sensitivity in detecting these microorganisms, facilitate detection in smaller samples or samples with lower microbial loads as compared with conventional techniques. Furthermore, the methods and media of the present invention have been used to successfully culture microorganisms that exhibit little or no detectable growth in mammalian culture media.

In particular embodiments, the sample or culture is passed through a size-excluding filter or filters (e.g., a 0.2 :m, a 0.45 :m, and/or a 1.2 :m filter).

A filtration step may be particularly advantageously employed with mixed cultures, e.g., to facilitate the growth and detection of a slower-growing species by removing faster-growing organisms that may be differentiated by size. Filtration may also used to assist in characterizing and identifying the organism based on size.

Those skilled in the art will appreciate that the length of time to culture the microorganism depends on the particular microorganism, culturing conditions, and the intended use of the culture. Particular microorganisms may exhibit rapid growth and may be detectable (e.g., by turbidity) within about 12–72 hours, or even less. Other, more slowly-growing microorganisms, may take as long as 1, 2, 3, 4, 5, or 6 weeks, or longer. In particular embodiments, slower-growing organisms may be cultured in medium of increased strength, e.g., 2×, 3×, 4×, 5×, or even 6×strength medium or more.

The present invention also provides pure or substantially pure (e.g., greater than about 80%, 85%, 90%, 95%, 98%, 99% or more pure) cultures of microorganisms isolated using the inventive methods and/or media.

Cultures of the microorganisms may advantageously be used to produce whole microorganisms, extracts or protein preparations that may be used to produce antibodies (e.g:, for vaccines or for diagnostic reagents, etc.).

As a further aspect, the present invention provides a method of detecting a microorganism, as defined hereinabove, in a sample, comprising culturing the sample containing the microorganism in a culture medium according to the invention (as described herein), and detecting the cultured organism. The organism may be detected by any method known in the art, including but not limited to, visual inspection, colony isolation, spectrophotometric methods (including colorimetry and measurement of optical density), staining, turbidity measurements, measurement of total cellular DNA and/or protein, impedance of an electrical field, bioluminescence, carbon dioxide, oxygen or ATP production or consumption, and the like.

Proteins and other compounds can be detected and/or quantified using standard analytical techniques such as chromatography, gel separation techniques, and the like. Likewise, methods of detecting nucleic acids are well-known in the art and include specific hybridization to probe sequences and amplification methods (e.g., polymerase chain reaction, strand displacement amplification, etc.). Carbohydrates can be detected by any method known in the art, including but not limited to, carbohydrate-specific staining (e.g., lectins or anthrone-based assays), spectrophotometric methods with dyes or copper, $A_{205}$ measurements, or gas-liquid chromatography.

Alternatively, immunoassays relying on specific binding to an antibody or receptor may be employed. Such methods typically involve a radiolabeled, fluorescent or other detectable moiety (e.g., a dye or intercalator such as acridine orange for DNA). Measurements may also be determined using labels that produce signals detectable by spectrophotometry (including colorimetry and measurement of optical density), x-ray diffraction or absorption, magnetism, or enzymatic activity. Chemiluminescence and fluorescence lifetime measurements may also be utilized. Suitable labels include fluorophores, chromophores, radioactive isotopes, electron-dense reagents, enzymes, and ligands having specific binding partners (e.g., biotin-avidin). Alternatively, a flow-through assay such as those that employ surface plasmon resonance detection may be used.

In particular preferred embodiments, the microorganism may be detected by detection of microbial nucleic acids, e.g., by direct sequencing, PCR, hybridization to probes, and the like.

Any measurement tool known in the art may be used to take measurements as described above, e.g., a spectrophotometer for absorption or calorimetric measurements, a fluorometer or flow cytometer for fluorescence measurements, a scintillation or gamma counter for radioactive measurements, and an automated cell counter, automated plate counter, or manual plate counter for cell number measurements. As a further example, a microwell reader can be used for fluorescence, absorbance or calorimetric measurements.

Methods of detecting microorganisms are particularly useful for quality control screening of organs and tissues (e.g., for organ transplant) or products produced from biological sources, e.g., blood products, including blood proteins. The inventive media may also be used to detect infections in animal products, e.g., meat, milk or eggs. For example, the present inventors have detected a high incidence of *Bartonella* and nanobacteria in a selected beef cattle population.

The present invention further encompasses methods of identifying a microorganism in a sample, comprising culturing a sample comprising the microorganism in a culture medium according to the invention and identifying the microorganism. Methods of identification and classification of microorganisms are well-known in the art and include the detection methods described above. Microorganisms may be identified according to size, shape, coloration, visual inspection of colonies, cell wall characteristics, growth on particular culture media, nutritional requirements, metabolic byproduct production and other metabolic characteristics, as well as requirements for oxygen, carbon dioxide, nitrogen, sulfur and the like. Microorganisms may also be identified by the presence of cell-surface or intracellular proteins or antigens. Molecular biology techniques may also be used to identify microorganisms based on nucleic acid characteristics. For example, direct sequencing, PCR or primers may be used to identify particular characteristic nucleic acid sequences (e.g., 16S RNA sequences).

The invention further provides a method of identifying a compound that binds to a microorganism, comprising culturing a sample comprising the microorganism in a cell-free medium and contacting the microorganism with the compound. The compound may, e.g., be an antibody or an antibiotic. The invention further provides methods of identifying compounds that enhance or inhibit growth of a microorganism.

An "antibiotic" as used herein is an antimicrobial agent that may be from a natural or synthetic source that inhibits, reduces or prevents the growth and/or viability (i.e., survival) of the microorganism. Microorganism growth and/or viability may be detected as described hereinabove.

The term "antibodies" as used herein refers to all types of immunoglobulins, including IgG, IgM, IgA, IgD, and IgE. The antibodies may be monoclonal or polyclonal, with monoclonal being preferred, and may be of any species of origin, including (for example) mouse, rat, rabbit, horse, or human, or may be chimeric antibodies. See, e.g., M. Walker et al., Molec. Immunol. 26, 403–11 (1989). The antibodies may be recombinant monoclonal antibodies produced according to the methods disclosed in Reading U.S. Pat. No. 4,474,893, or Cabilly et al., U.S. Pat. No. 4,816,567. The antibodies may also be chemically constructed by specific antibodies made according to the method disclosed in Segal et al., U.S. Pat. No. 4,676,980.

The term "antibody" as used herein also encompasses antibody fragments. Antibody fragments included within the scope of the present invention include, for example, Fab, F(ab')2, and Fc fragments, and the corresponding fragments obtained from antibodies other than IgG. Such fragments can be produced by known techniques.

The present invention further provides antibodies directed to microorganisms isolated in pure or substantially pure form by the inventive media and techniques. It is preferred that the antibody binds the microorganism with high affinity, e.g., with a dissociation constant of at least about $10^{-6}$, preferably at least about $10^{-7}$, more preferably at least about $10^{-8}$, still more preferably at least about $10^{-9}$. Alternatively stated, the antibody specifically binds to the microorganism (as opposed to non-specific interactions). As used herein, the term "specifically binds to the microorganism" is not intended to indicate that the antibody only binds to that microorganism (e.g., does not bind to other microorganisms), although in particular embodiments, this may be the case.

Polyclonal antibodies used to carry out the present invention may be produced by immunizing a suitable animal (e.g., rabbit, goat, etc.) with an antigen from the microorganism (e.g., a cell-surface protein or peptide), collecting immune serum from the animal, and separating the polyclonal antibodies from the immune serum, in accordance with known procedures.

Monoclonal antibodies used to carry out the present invention may be produced in a hybridoma cell line according to the technique of Kohler and Milstein, Nature 265, 495–97 (1975). For example, a solution containing the appropriate antigen may be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity. Monoclonal Fab fragments may be produced in Escherichia coli by recombinant techniques known to those skilled in the art. See, e.g., W. Huse, Science 246, 1275–81 (1989).

Antibodies specific to the microorganism may also be obtained by phage display techniques known in the art.

Antibodies as described herein may be conjugated to a solid support suitable for a diagnostic assay (e.g., beads, plates, slides or wells formed from materials such as latex or polystyrene) in accordance with known techniques, such as precipitation. Antibodies as described herein may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques. The term "antigenic equivalents" as used herein, refers to proteins or peptides which bind to an antibody which binds to the protein or peptide with which equivalency is sought to be established. Antibodies which are used to select such antigenic equivalents are referred to as "selection antibodies" herein.

The methods of culturing, detecting and/or identifying a microorganism described hereinabove may be advantageously employed in diagnostic methods for medical and/or veterinary applications. For example, a microorganism may be detected or identified in a sample taken from a subject. The presence of the microorganism in the sample may be associated with an increased risk of developing a disease state or disorder, as described hereinabove. The presence of the microorganism may also be associated with the existence of a disease state of disorder.

The Examples that follow are provided to illustrate particular embodiments of the present invention, and are not to be construed as limiting, thereof. Likewise, the media formulations described in the Examples are exemplary only. The concentration of the individual components of the disclosed formulations may be varied to optimize the media for growth of particular organisms depending, e.g., on the host species, age and condition of the host, type of tissue or fluid sample, and the organism to be cultured.

Thus, those of ordinary skill in the art will be able to, based on the guidance and teachings disclosed herein be able to modify (e.g., optimize) the inventive media for use in particular applications or with particular microorganisms.

In general, concentrations of the individual media components may range from about 0.01, 0.1, 0.25, 0.5 to about 2, 3, 5, 10, 20, 50, 100 or 500 times the concentrations provided above or in the Examples below. Further, particular media components may be optional and may be omitted altogether from the formulations of the invention. Likewise, particular combinations of media components may be extracted from the formulations provided in the Examples below, with the other components being omitted from the final medium.

EXAMPLE 1

Insect Growth Medium

Unless indicated otherwise, all reagents, chemical, and medium components were obtained from Sigma-Aldrich, Saint Louis, MO.

Liquid Insect Growth Medium:

Grace's Liquid and Hink's Liquid Insect Growth Media (both indicated as "IGM" herein) were obtained from Celigro® (www.cellgro.com). These media are typically used, e.g., for growth of cultured Drosophila cells. The composition of Grace's and Hink's media are shown in Table 1.

TABLE 1

| | Constituent | Grace's mg/L Amount | Hink's mg/L Amount |
|---|---|---|---|
| 1 | Calcium Chloride, Anhydrous | 750.00 | — |
| 2 | Calcium Chloride, Dihydrate | — | 1324.60 |
| 3 | Potassium Chloride | 4100.00 | 2240.00 |
| 4 | Magnesium Chloride | 1067.86 | 1067.86 |
| 5 | Magnesium Sulfate | 1357.67 | 1357.67 |
| 6 | Sodium Bicarbonate | 350.00 | 350.00 |
| 7 | Sodium Phosphate, Monobasic | 1013.00 | 1013.00 |
| 8 | Fructose | 399.00 | 399.00 |
| 9 | Fumaric Acid | 54.00 | 54.00 |
| 10 | Dextrose | 699.00 | 699.00 |
| 11 | α-Ketoglutaric Acid | 369.00 | 369.00 |
| 12 | L-Malic Acid | 670.00 | 670.00 |
| 13 | Succinic Acid | 59.00 | 59.00 |
| 14 | Sucrose | 26680.00 | 26680.00 |
| 15 | Lactalbumin Hydrolysate | — | 3330.00 |
| 16 | Yeastolate | — | 3330.00 |
| 17 | β-Alanine | 200.00 | 200.00 |
| 18 | L-Alanine | 225.00 | 225.00 |
| 19 | L-Arginine HCl | 699.00 | 699.00 |
| 20 | L-Asparagine $H_2O$ | 397.70 | 397.70 |
| 21 | L-Aspartic Acid | 350.00 | 350.00 |
| 22 | L-Cystine 2HCl | 28.68 | 28.68 |
| 23 | L-Glutamic Acid | 600.00 | 600.00 |
| 24 | L-Glutamine | 600.00 | 600.00 |
| 25 | Glycine | 649.00 | 649.00 |
| 26 | L-Histidine, Free Base | 2500.00 | 2500.00 |
| 27 | L-Isoleucine | 50.00 | 50.00 |
| 28 | L-Leucine | 75.00 | 75.00 |
| 29 | L-Lysine HCl | 625.00 | 625.00 |
| 30 | L-Methionine | 50.00 | 50.00 |
| 31 | L-Phenylalanine | 150.00 | 150.00 |
| 32 | L-Proline | 349.00 | 349.00 |
| 33 | DL-Serine | 1099.00 | 1099.00 |
| 34 | L-Threonine | 174.00 | 174.00 |
| 35 | L-Tryptophan | 100.00 | 100.00 |
| 36 | L-Tyrosine 2Na $2H_2O$ | 72.63 | 72.63 |
| 37 | L-Valine | 100.00 | 100.00 |
| 38 | d-Biotin | 0.01 | 0.01 |
| 39 | D-Ca Pantothenate | 0.02 | 0.02 |
| 40 | Choline Chloride | 0.20 | 0.20 |
| 41 | Folic Acid | 0.02 | 0.02 |
| 42 | myo-Inositol | 0.02 | 0.02 |
| 43 | Niacin | 0.02 | 0.02 |
| 44 | PABA | 0.02 | 0.02 |
| 45 | Pyridoxine HCl | 0.02 | 0.02 |
| 46 | Riboflavin | 0.02 | 0.02 |
| 47 | Thiamine HCl | 0.02 | 0.02 |

IGM Agar Plate Preparation:

Make 2% agarose, sterilize by autoclaving at 121° C., cool, and mix 1:1 (v/v) with IGM to produce a 1% agarose solution.

IGBA Agar Plate Preparations:

Prepared as for IGM agar plates, with addition of 10% rabbit blood.

IGTBA Agar Plate Preparations:

Make a 2×trypticase soya agar (TSA) in IGM, sterilize by autoclaving at 121° C., cool, and mix 1:1 (v/v) with IGM+10% rabbit blood to make a 1×TSA solution.

EXAMPLE 2

Culturing of Blood Sample 1. 1 ml of blood/EGTA is added to 9 ml of insect growth medium as described in Example 1. If clot formation starts, disperse clot by agitation.
2. Incubate mixture at 37° C. and in 5% $CO_2$ until it curdles.
3. Add 0.5 ml of a sterile 7.5% solution of $NaHCO_3$ to buffer the solution.
4. Plate out on (a) IGM agar, (b) IGM+10% rabbit blood agar (IGBA), (c) IGF+trypticase soya+10% rabbit blood agar (IGTBA), all as described in Example 1.
5. Can plate sample directly onto agar plates or can first pass through a filter of desired size, e.g., 0.2 :m, 0.45 :m, and/or 1.2 :m filters. This may be accomplished by passing the culture through the desired filter and holding the filter over the agar plate.
6. Incubate plates at 37° C. in 5% $CO_2$.
7. Pick and transfer isolated colonies to the same medium.

Alternative A:

Culturing is carried out as described in Steps 1–7 above, except that 1 ml of blood/EGTA is added to 1 ml of insect growth medium in step 1.

Alternative B:

Culturing is carried out as described in Steps 1–7 above, except in step 1 the blood is allowed to digest for 48 hr at 37° C. in 5% $CO_2$ and then an equal volume of insect growth medium is added.

EXAMPLE 3

Filtering Blood prior to Culturing on IGM

1. Blood is passed through a filter(s) of desired size, e.g., 0.2 :m, 0.45 :m, and/or 1.2 :m filters.
2. Blood is then diluted 1:10 with IGM as described in Example 1. Note: with a very small diameter filter, it may be necessary to perform dilution step prior to filtration.
3. Incubate 10% blood sample at 37° C. in 5% $CO_2$ for 48 hr. Positive samples will typically show turbidity within 24–48 hr.
4. Add 0.5 ml of a sterile 7.5% solution of $NaHCO_3$.
5. Follow steps 4–7 as in Example 2.

EXAMPLE 4

Culturing Cerebrospinal Fluid (CSF) or Urine on IGM

1. Add 1 ml of urine or CSF to IGM as described in Example 1.
2. Incubate at 37° C. and in 5% $CO_2$ until turbidity appears.
3. Add 0.5 ml of a sterile 7.5% solution of $NaHCO_3$ to buffer the solution.
4. Follow Steps 4–7 as in Example 2.

EXAMPLE 5

Filtering Urine or CSF prior to Culturing on IGM

1. Urine or CSF sample is passed through a filter(s) of desired size, e.g., 0.2 :m, 0.45 :m, and/or 1.2 :m filters.
2. Blood is then diluted 1:10 with IGM as described in Example 1. Note: with a very small diameter filter, it may be necessary to perform dilution step prior to filtration.
3. Incubate 10% blood sample at 37° C. in 5% $CO_2$ for 48 hr. Positive samples will show turbidity within 24–48 hr.
4. Add 0.5 ml of a sterile 7.5% solution of $NaHCO_3$.
5. Follow steps 3–7 as in Example 2.

EXAMPLE 6

Detection of Microorganisms in Mammalian Samples

The media and methods described in Examples 1–5 above, have been used to culture and detect or identify numerous organisms in a variety of samples as set forth below:
  *Afipa* in CNS fluid from a dog (an α-proteobacteria)
  *Bartonella* from bovine and canine blood
  *Streptococcus thermophilis* from canine pleural fluid
  *Corynebacterium* from feline blood
  *Burkholdrea pickettii*
  Hydrogenophagia species
  *Pseudomonas plecoglossicida* (γ-Proteobacteria)
  *Mycobacterium kansasii*
  *Bacillus clausii*
  *Streptococcus pneumonia*
Microorganisms have been cultured using the foregoing techniques and media in samples from canine and/or feline subjects with the following conditions:
  culture-negative endocarditis
  hypertensive cats
  feline urologic syndrome
  feline chylothorax fluid
  canine pleural effusion
  abdomen transudates
  inflammatory CSF
  cancer
  protein-losing nephropathy
  hyperadrenalcorticism
  chronic hepatopathy
  mastitis
  pyelonephritis
  hypertension
  polyarthritis
  immune-mediated hemolytic anemia and/or thrombocytopenia

EXAMPLE 7

Basal EBSS Media

Many media are currently used to facilitate the growth of microorganisms of clinical importance. These media include blood agar, nutrient agar, and brain heart infusion agar. However, heat action (e.g., for sterilization) destroys vitamins or amino acids. Reproducibility is variable from lot to lot depending upon, e.g., the blood source, or the soya composition which may vary from season to season or from one day to another.

Moreover, organisms may become "defective" due to injury or stress upon introduction into the host, e.g., as a result of anti-bacterial mechanisms by the host, antibiotics or surfactant production by the lung. For example, the cell wall of the organism may be damaged or even destroyed. In addition, transport mechanisms or cellular metabolic pathways may be disrupted as a result of injury or stress to the organism. These defective metabolic functions may include defects in the synthesis of TCA cycle enzymes, amino acids, or cell wall enzymes, or these organisms may have become dependent on the metabolites supplied by the host. Therefore, these microbes may not have effective expression of enzymes to support growth in vitro. It is likely that this phenotypic and/or genetic plasticity may arise by selection for microbial cells that can survive in the body under stress, such as specific nutrient limitations (e.g., iron), or in the presence of antimicrobial factors.

Alternatively, the organism may form a viable, but non-culturable microbe, which is a metabolically inactive form of the organism. Defective organisms that have suffered stress, or metabolically-inactive microbes, are more resistant or refractory to standard culturing and isolation techniques.

Currently available media may be deficient in components required for the growth of these fastidious organisms (as described above). The EBSS media described herein have been formulated to address the more stringent needs of these organisms. In general, particular components that are important for optimal growth of the organism are supplied in sufficiently high concentrations so as to allow microbial cells that are surviving but have developed defective transport mechanisms or other defective metabolic functions, to grow in the laboratory.

This Example describes the basal formulation of a novel liquid culture media (EBSS Media). The basal EBSS medium comprises the ingredients in Table 2. The ingredients from 43–61 are optional and may be included in particular media formulations. For example, typically all three sugars (ingredients 57–59 would not be used in the same formulation). Variations in the medium components will be made depending on a number of factors, e.g., host species, age and condition of the host, type of tissue or fluid sample, organism to be cultured.

As a further illustration, in particular clinical settings the salt concentration has been increased or varied the relative concentrations of the salt components, as these factors are important for clinical samples. Thus the salt concentration may vary to accommodate the conditions in a particular clinical sample.

The components of the basic formulation of EBSS Medium provide a unique combination of ingredients that have not previously been found in currently available media. In general, the concentrations of particular ingredients in the EBSS basal medium are also unique, as they are considerably higher than concentrations typically used in microbiological media. For example, ingredients 43–60 in Table 2 (e.g., glutathione, vitamin K, cocarboxylase, coenzyme A, hemin, ascorbic acid, tyrosine, hydroxy proline, threonine, histidine, and all of the deoxynucleosides) are included in particular formulations of the inventive media at higher concentrations than found in previously known media. In addition, particular ingredients such as coenzyme A, cocarboxylase, β-NAD, β-NADP and vitamin K are not found in conventional mammalian culture media.

The individual components (or class of components) may be included in the EBSS basal medium at various concentrations depending upon their function in the medium and the particular clinical sample. For example, glutathione is typically included at a relatively high concentration so as to combat oxidative damage. Vitamin $K_1$ is also anti-oxidative and is more effective than glutathione in some microorganisms in facilitating growth. All of the nucleotides are typically included in the formulation so as to facilitate diffusion of the compounds into microorganisms that have deficient or absent transport systems. Likewise, β-NAD and β-NADPH, are provided in high concentrations so as to boost their diffusion through the cell walls/membrane of microbes. Coenzyme A and cocarboxylase are included because these molecules facilitate $CO_2$ assimilation and vitamin synthesis.

TABLE 2

| | Constituent | Amount (g/L) |
|---|---|---|
| 1 | $CoCl_2.6H_2O$ | 0.00005 ± 0.00005 |
| 2 | $CuCl_2$ anhydrous | 0.000158 |
| 3 | $FeSO_4.7H_2O$ | 0.00055 ± 0.0005 |
| 4 | $MgSO_4$ anhydrous | 0.918 |
| 5 | $MgCl_2.4H_2O$ | 0.00002 |
| 6 | $(NH_4)_6Mo_7O_{25}.4H_2O$ Ammonium Molybdate | 0.00004 |
| 7 | KCl | 0.4 |
| 8 | $Na_2HPO_4$ | 1.008696 |
| 9 | $ZnCl_2$ | 0.0004 |
| 10 | β-Alanine | 0.5 |
| 11 | L-Arginine.HCl | 0.8 |
| 12 | L-Aspartic Acid | 1.3 |
| 13 | L-Asparagine | 1.3 |
| 14 | L-Cystine.2HCl | 0.13 |
| 15 | L-Cysteine free base | 0.06 |
| 16 | L-Glutamic Acid | 1.5 |
| 17 | Glycine free base | 0.2 |
| 18 | L-Histidine free base | 0.4 |
| 19 | Hydroxy-L-Proline | 0.8 |
| 20 | Isoleucine | 0.75 |
| 21 | L-Leucine | 0.25 |
| 22 | L-Lysine.HCl | 0.7 |
| 23 | L-Methionine | 1.0 |
| 24 | L-Phenylalanine | 1.0 |
| 25 | L-Proline | 0.5 |
| 26 | DL-Serine | 0.4 |
| 27 | L-Threonine | 0.35 |
| 28 | L-Tryptophan | 0.1 |
| 29 | L-Tyrosine disodium salt | 0.72 |
| 30 | L-Valine | 0.5 |
| 31 | L-Ascorbic Acid | 0.05 ± 0.05 |
| 32 | p-Aminobenzoic Acid (PABA) | 0.00032 |
| 33 | d-Biotin | 0.00016 |
| 34 | Choline Chloride | 0.02 |
| 35 | Folic Acid | 0.00008 |
| 36 | myo-Inositol | 0.0004 |
| 37 | Niacin | 0.00016 |
| 38 | D-Panthothenic Acid Hemicalcium Salt | 0.00002 |
| 39 | Pyridoxal.HCl | 0.0004 |
| 40 | Riboflavin | 0.00008 |
| 41 | Thiamine.HCl | 0.00008 |
| 42 | Vitamin $B_{12}$ | 0.00024 |
| 43 | Coenzyme A | 0.01 |
| 44 | Cocarboxylase | 0.2 |
| 45 | Thymidine | 0.08 |
| 46 | Uridine 5'-Triphosphate Sodium Salt | 0.08 |
| 47 | 2'-Deoxyadenosine | 0.08 |
| 48 | 2'-Deoxyguanosine | 0.0083 |
| 49 | 2'-Deoxycytodine.HCl | 0.0083 |
| 50 | 5-Methyl-2'-Deoxycytidine | 0.0001 |
| 51 | β-Nicotinamide Adenine Dinucleotide (β-NAD) | 0.02 |
| 52 | β-Nicotinamide Adenine Dinucleotide Phosphate, Reduced Form (β-NADPH) | 0.005 |
| 53 | Glutathione | 0.04 ± 0.05 |
| 54 | HEMIN | 0.005 to 0.05 |
| 55 | Vitamin $K_1$ | 0.01 |
| 56 | Acyl Homoserine Lactone | 0 to 0.05% |
| 57 | D-Glucose | 0.25% |
| 58 | Maltose | 0.1% |
| 59 | Sucrose | 0.16% |
| 60 | Yeastolate | 0.4% |

TABLE 2-continued

| | Constituent | Amount (g/L) |
|---|---|---|
| 61 | HEPES pH 6.0 | 6.0 |
| 62 | NaOH to adjust pH to 7.2 | |

EXAMPLE 8

EBSS Formulation 2 Medium

EBSS Formulation 2 Medium combines the constituents from the Basal Medium (Table-2) with a unique sugar formulation (Table 3) that is particularly suited, e.g., for growth of microbes found in blood, synovial fluids, or tissue samples. As far as the inventors are aware, this sugar formulation is not found in any previously available media. Alternatively, in other embodiments of the invention, the sugar formulation of Table 3 may be used alone or in combination with any other suitable basal medium other than EBSS Basal Medium.

Ribose, the central metabolite of the pentose phosphate pathway is an important sugar for allowing microbial growth in red blood cells (RBCs). As RBCs do not have predominant EMP pathway activity, free sugar molecules that might be present in RBCs would be produced by the pentose phosphate pathway. Microbes that grow in RBCs that are generally difficult to culture in vitro may be advantageously grown in this formulation, which contains sugars that are found in RBCs.

N-Acetyl-D-glucosamine and N-acetylmuramic acid were included in this formulation as they are building blocks of cell walls in bacteria. Glycerol, which can be converted directly to energy via expenditure of only one ATP molecule, was incorporated so as to facilitate the growth of defective or injured microbes. The glucose concentration is relatively high to allow for simultaneous growth of multiple microbes that may be present in body fluid or tissue samples.

TABLE 3

| | Constituent | Amount |
|---|---|---|
| 1 | N-Acetylmuramic Acid | 0.1% ± 0.2 |
| 2 | Ribose | 0.5% |
| 3 | N-Acetyl-D-Glucosamine | 0.25% |
| 4 | D-Glucose | 0.5% |
| 5 | Glycerol | 0.1% ± 0.2 |

EXAMPLE 9

EBSS Formulation 3 Medium

EBSS Formulation 3 Medium, which combines the constituents from the EBSS Basal Medium (Table 2) with the components of Table 4 has a unique formulation that is well-suited, e.g., for growth of microbes that do not require sugars for growth. The acids listed in Table 4 can be used as a carbon source as well as a nitrogen source (ammonium salt formation due to pH adjustment with $NH_4OH$). As these acids are generated through the TCA cycle, they are generally found in the cytoplasm surrounding the host cell mitochondria. The microbe may become adapted in the host to grow in the presence of these acids, and may be cultured more readily in their presence.

The concentrations of the acids in the EBSS Formulation 3 Medium are relatively high. In addition, several different acids were incorporated into the medium to provide a variety of alternative carbon sources to support microbial growth.

Alternatively, in other embodiments of the invention, the acid formulation of Table 4 may be used alone or in combination with any other suitable basal medium other than EBSS Basal Medium.

TABLE 4

| | Constituent | Amount |
|---|---|---|
| 1 | Malic Acid | 0.005% ± 0.05 |
| 2 | Fumaric Acid | 0.1% |
| 3 | α-Ketoglutaric Acid | 0.003% ± 0.05 |
| 4 | Aspartic Acid | 0.65% |
| 5 | Succinic Acid | 0.1% |
| 6 | Pyruvic Acid | 0.1% |
| 7 | Citric Acid | 0.98% |
| 8 | Adjust pH with NH$_4$OH to 7.2 | |

EXAMPLE 10

EBSS Formulation 4, 5, 6, 7, and 8 Media

EBSS Formulation 4, 5, 6, 7, and 8 Media which combines the constituents from the EBSS Basal Medium (Table 2) with the formulations of Table 5, Table 6, Table 7, Table 8, Table 9, respectively, provide for growth of microorganisms that are found in body fluids especially in transudates, modified transudates, and chylous effusions with relatively low protein concentrations (transudates have very low protein concentrations; chylos fluid has a much higher protein concentration, but still lower than blood). Alternatively, in other embodiments of the invention, the formulations of Table 5, Table 6, Table 7, Table 8 and Table 9 may be used alone or in combination with any other suitable basal medium other than EBSS Basal Medium.

Presumably, these microorganisms maintain their osmotic balance within the low protein environment by the utilization of membrane strengthening or stabilization reagents. These microbes typically pass through 0.2 micron filters and thus most probably lack a cell wall. To support the growth of these microorganisms in protein-free media, lipid components, soluble as well as insoluble (made soluble with a surfactant), have been added to EBSS Basal Media (Table 5, Table 6, and Table 7).

To specifically enhance the growth of microbes that are found in tissues that contain higher concentrations of lipid material such as the nervous tissue, 10 mL of the Lipid Medium Supplement of Table 5 is added to 1 liter of EBSS Basal Medium.

Pluronic series surfactants are useful in this context as these surfactants vary in their detergency and emulsification properties. In addition, pluronic series surfactants are non-toxic even at high concentrations. It has been found that these surfactants can dissolve lipid material without causing toxicity or inhibitory effects on microbial growth. Pluronic F 68 is particularly desirable as it is found in the best detergency and foaming regions. Pluronic R and Pluronic L 62 are also useful.

TABLE 5

| | Constituent | Amount |
|---|---|---|
| 1 | Pluronic F-68 | 100 g/L |
| 2 | Lipid Mixture (see below) | 100 mL/L |
| | Lipid Mixture Constituents | Amount (g/L) |
| 1 | Cholesterol | 4.5 |
| 2 | Cod Liver Oil Fatty Acid Methyl Esters | 10.0 |
| 3 | Polyoxyethylenesorbitan Monooleate | 25.0 |
| 4 | D-α-Tocopherol Acetate | 2.0 |

To specifically enhance the growth of microbes that are inhibited by pluronic series surfactants or by cod liver fatty acid methyl esters, the constituents of Table 6 may be directly added to EBSS Basal Medium (Table 2) to produce formulation 5. This formulation is particularly useful for microbes that may be inhibited by the components in formulation 4 (EBSS Basal+the components of Table 5), e.g., because of their cell wall composition.

TABLE 6

| | Constituent | Amount |
|---|---|---|
| 1 | Phosphatidylcholine | 0.06 g/L |
| 2 | Tween 80 | 0.5 g/L |
| 3 | Cholesterol | 0.045 g/L |

To specifically enhance the growth of microbes that are inhibited by any surfactant, the constituents of Table 7 (Soluble Lipid Supplement) to produce formulation may be directly added to EBSS Basal Medium.

TABLE 7

| | Constituent | Amount |
|---|---|---|
| 1 | Phosphatidylcholine | 0.01 g/100 ml |
| 2 | Cholesterol Soluble | 0.04 g/100/ml |
| 3 | Cholesterol Insoluble | Trace amounts - remove remaining insoluble material |
| 4 | Cod Liver Oil Fatty Acid Methyl Esters | 0.01 g/100 ml |

Other possible media components include phosphatidyl inositol, phosphatidyl glycerol, phosphatidyl ethanolamine (plasmalogen), and phosphatidyl-L serine. Lipids that are found in brain tissues are particularly of interest, including, but not limited to phosphatidyl serine, phosphatidyl inositol, cerobramide, phophoglycolic acid, phosphatidyl ethanolamine, phosphatidyl choline, cerebrosides (including different chain lengths), and glycosylated cerebrosides.

Several considerations were involved in developing a medium formulation particularly intended for culturing microorganisms in cerebrospinal fluid (CSF). For microorganisms to pass through the blood-brain barrier into CSF, the microbes would have to pass through a 0.2 micron interstitial space. These microbes would theoretically require a relatively high concentration of fatty acids for cell membranes, as they might lack cell walls, and fatty acids are found in high concentration in nervous tissue. Therefore, to isolate these types of microorganisms, lipid formulation 5 (Table 6) along with sugar and acid formulations 2 and 3, respectively, were added to the EBSS Basal Medium to constitute formulation 7. Sufficient concentrations (0.5 g/L) of tween 80 were used in order to allow for increased diffusion of fatty acids into the microbial cells.

Formulation 8 medium combines the formulations of Tables 3 and 4 to the EBSS Basal Medium. Thus, formulation 8 contains both sugars and acids. This medium may be used to simultaneously culture organisms that grow on either formulation 2 or formulation 3 medium. In addition, this formulation may be used to culture organisms that have requirements for both sugars and acids.

EXAMPLE 11

Comparison of EBSS Media to Commercially Available Media

EBSS Media were compared to protein-free tissue culture media such as IPL 41 base medium and DS2 medium (Cellgro), which simulate the conditions in the body fluids. *Escherichia coli, Aeromonas hydrophila, Bordetella bronchoseptica, Salmonella typhimurium, Pseudomonas aeruginosa, Proteus mirabilis, Bartonella weisii, B. clarridgiae, B. vinsonii* subspecies *berkhoffii*, and *B. henselae* cultures were grown overnight on Blood Agar plates at 37° C. to achieve log phase growth. Cells were subsequently scraped from the Blood Agar plates and inoculated into 2 ml of EBSS Basal Medium. Equal quantities (0.2 ml of microbial suspension) of each organism (Table 8) were added to each formulation. The growth obtained for each organism grown in different formulations was visually compared and subjectively quantitated as an increase or decrease in growth intensity (indicated by plus sign). All *Bartonella* cultures were grown in the formulations for one month and results were noted after one month. For the other microorganisms results were noted after 24 hr.

TABLE 8

| Formulation | *E. coli* | *P. aeruginosa* | *P. mirabilis* | *A. hydrophila* | *B. bronchoseptica* |
|---|---|---|---|---|---|
| IPL 41 | +++ | ++++ green color | +++ | +++ | +++ |
| DS2 | +++ | ++++ finely dispersed growth | ++++ | ++++ | ++ |
| RPMI | +++ yellow color | + | +++ yellow color | ++ no change in pink color | + no change in pink color |
| EBSS Basal Medium | +++ | ++++ | ++++ | +++ | +++ |
| Number 2 | ++++ | ++++ | +++ | ++++ | +++ |
| Number 3 | +++++ | +++++ | ++++ | ++++ | ++ |
| Number 8 | ++++ | +++++ clumpy growth | +++++ | ++++ | +++ |
| Number 4 | +++ | +++ | ++ | ++ | ++ |
| Number 5 | +++ | +++ | ++ | ++ | ++ |
| Number 6 | +++ | +++ | ++ | ++ | ++ |
| Number 7 | +++ | +++ | ++ | ++ | ++ |

| Formulation | *S. typhimurium* | *B weisii* | *B. vinsonii* subspecies *berkhoffii* | *B. henselae* | *M. kansasii* | *B. quintana* |
|---|---|---|---|---|---|---|
| IPL 41 | +++ | + | NA | NA | NA | |
| DS2 | +++ | + | 0 | trace | ++ | trace |
| RPMI | ++ yellow color | trace | − | − | Trace | − |
| EBSS Basal Medium | ++ | trace | trace to negative | trace | + | trace |
| Number 2 | ++++ | trace | − | − | − | − |
| Number 3 | ++++ | − | − | − | Trace | ++ to trace |
| Number 8 | ++++ | trace to negative | − | − | trace to negative | − |
| Number 4 | +++ | trace | trace to negative | trace | − | + to trace |
| Number 5 | +++ | trace | trace to negative | − | ++ | + to trace |
| Number 6 | +++ | + | trace to negative | trace | ++ | + to trace |
| Number 7 | +++ | + | trace to negative | − | − | − |

Trace indicates that the growth was less than +.

It was noted that *B. weisii* could be revived from its frozen state in the liquid EBSS basal medium. As demonstrated in Table 8, performance of EBSS media, in terms of growth of the various microorganisms tested, is superior to DS2 and IPL 41.

EXAMPLE 12

Isolation of Microorganisms from Clinical Samples on EBSS Basal Medium

Sample Preparation. Irrespective of the clinical sample the inoculations are done as follows (blood is used here as an illustrative example). 1 mL of an EDTA blood sample is added to 9 mL of EBSS Basal Medium. If clot formation starts, the clot is broken up by shaking. Flasks are incubated at 37° C. and in 5% $CO_2$ until the blood curdles (0.5 mL of sterile 7.5% $NaHCO_3$ is added after curdles appear so that the microorganisms survive for an extended period of time). The liquid is plated on EBSS agar, EBSSBA (EBSS agar supplemented with 10% rabbit blood), and on EBSSTBA (EBSS supplemented with trypticase soya agar and 10% rabbit blood). Plates are incubated under conditions similar to those for liquid medium and the isolates maintained on the same plates. Variation in the relative volume of clinical sample to medium can be used in cases where no growth has been observed with a 1:10 ratio of inoculum to medium. For example, a ratio of 1:1 may be used and the organisms can be initially allowed to grow in the blood itself for an extended period of time. Subsequently, the organisms can be diluted with medium and plated.

If the liquid is filtered, filters such as 0.2 microns, 0.45 microns or 1.2 micron may be used. The filter is held directly above the culture plate to catch the filtrate. After filtration, plates are typically incubated at 37° C. in 5% $CO_2$ for 48 hr. Incubation for 24 to 48 hr is sufficient to isolate fast growing organisms, and periods of up to one month (or longer) may be required for slow growing organisms like the *Bartonella* spp.

Media Preparation

EBSS agar plate preparation: Prepare 2% Agarose, sterilize by autoclaving at 121° C. and mix with cooled 2×EBSS liquid medium to generate a final concentration of 1% Agarose and 1×EBSS. Pour the plates.

EBSSTBA agar plate preparations: Prepare 2×trypticase soya agar (TSA), autoclaving, cool and mix with 10% rabbit blood and 2×EBSS.

EBSSBA agar plate preparations: Similar to EBSS, except 10% rabbit blood is included.

DNA Isolation. To confirm the identity of the microorganisms isolated from the clinical samples, DNA is isolated, the 16S RNA genes are PCR amplified and sequenced. DNA is isolated from organisms grown in liquid culture or on plates using the DNA minikit supplied by Qiagen, Inc. (Valencia, Calif.). The protocol is that for DNA isolated from blood and body fluids as supplied by the manufacturer.

PCR Amplification. Primers PC5A: 5'-CCTTGTTAC-GACTTCACCC and PO-C: 5'-AGAGTTTGATCCTGG have been used previously for 16S RNA gene amplification. Primers were from Integrated DNA Technologies, Inc. (IDT, Coralville, Iowa). PCR amplification is performed in the following 50 µL reaction volume: 1 µM each primer, 3 mM $MgCl_2$, 200 µM of each four deoxynucleotides, 10 mM Tris HCl pH 8.3, 50 mM KCl, 0.001% gelatin (w/v), and 1.25 units of Amplitaq Gold Polymerase (PE Applied Biosystems, Foster City, Calif.). Thermocycler conditions are: 95° C. for 10 min, 35 cycles at 94° C. for 1 minute, 53° C. for 1 minute, 72° C. for 2 minutes, followed by a 72° C. extension for 5 minutes. DNA is analyzed on a 1% agarose gel, stained with ethidium bromide, and photographed.

*DNA Sequencing.* DNA from three strains is amplified by the above method and used for DNA sequencing. DNA from all three strains is sequenced at the Central Sequencing Laboratory, University of North Carolina at Chapel Hill. The samples are prepared according to the sequence facility's instructions. The primers used are obtained from Integrated DNA Technologies, Inc. (IDT, Coralville, Iowa). Both strands of DNA from all three strains are sequenced. Forward primers used previously are:

| | |
|---|---|
| POC: | AGAGTTTGATCCTGG |
| P1: | ACTCCTACGGGAGGCAGCAGT |
| P3MOD: | ATTAGATACCCTGGTAGTCC |
| P4: | GAGGAAGGTGGGGATGACGTCAA |

Reverse primers were:

| | |
|---|---|
| PC5A: | CCTTGTTACGACTTCACCC |
| PC4: | TTGACGTCATCCCCACCTTCCTC |
| PC3: | GGACTACCAGGGTATCTAAT |
| PC1: | ACTGCTGCCTCCCGTAGGAGT |

EXAMPLE 13

Isolation of Microorganisms from Clinical Samples on DS2 Insect Growth Medium

Microorganisms isolated from various clinical samples from canine and feline patients and grown on DS2 insect growth medium are shown in Table 9.

TABLE 9

| Patient and Clinical Sample | Disease Condition and Treatment | Growth on Blood Agar for One Month | Growth in DS2 Basal Medium by Microscopic Examination | 16S RNA Amplification | Tentative Identification by Partial or Complete Sequencing |
|---|---|---|---|---|---|
| Subject 1 Canine, Synovial Fluid | Neutrophilic Arthritis | − | + cocci | + | Multiple Organisms, plate isolate *S. cohenii* |
| Subject 2 Canine, CSF | Granulomatous Meningoencephalitis, Head Paresis | − | ++++ cocci | + | |
| Subject 3 Feline, Blood | IMHA 3 Years, Hypergamma Globulinemia Splenomegaly | − | +++ rods | + | Plate isolate:uncultured *Corynebacterium* spp, *S. pneumoniae* |
| Subject 4, Canine, Chest Fluid | Plural Effusion, Lung Lobe Torsion, Denver Shunt, Thick Pericardium | − | ++ pellets | + | *Mycobacterium kansasii* |
| Subject 5 Feline, Chylous Fluid | Fever, Chylothorax, Pyrothorax, Eosinophilia, Basophilia | − | + | + | Multiple organisms and yellow growth |
| Subject 6 Canine, Abdominal Fluid | Ascites, Transudate, ANA, Protein Losing Glomerulonephropathy | − | ++++ EM showed cocobacillary rods | + | Multiple organisms Clone: Comamomonas or Hydrogenophagia |
| Subject 7 | Plural Effusion, Modified | − | + | + | MultipleClone: |

TABLE 9-continued

| Patient and Clinical Sample | Disease Condition and Treatment | Growth on Blood Agar for One Month | Growth in DS2 Basal Medium by Microscopic Examination | 16S RNA Amplification | Tentative Identification by Partial or Complete Sequencing |
|---|---|---|---|---|---|
| Canine, Abdominal Fluid | Transudate | | coccobacillary rods | | *Burkholderia pickettii* |

EXAMPLE 14

Isolation of Microorganisms from Clinical Samples that Show Inhibition in the Presence of Sugars Some microorganisms may be inhibited in their growth in the presence of sugars. For these organisms (which may show insufficient growth in any of the EBSS formulations described above), the EBSS basal medium (Table 2) is modified to omit simple sugar components. Optionally and preferably, this medium is supplemented by the addition of acids (Table 4) and lipid components (Tables 5, 6 and/or 7). EBSS media containing acids and lipids, but lacking simple sugars, may advantageously be used to culture microorganisms such as *Bartonella* spp.

Although the foregoing invention has been described in some detail by way of illustration and example for purposes of clarity of understanding, it will be obvious that certain changes and modifications may be practiced within the scope of the appended claims.

That which is claimed is:

1. A culture medium for growing a fastidious microorganism wherein the culture medium comprises:
   free amino acids including glutamine at a concentration of 300 to 6000 mg/l;
   organic acid as a carbon source;
   hemin;
   yeast extract;
   nucleotides;
   vitamins;
   acyl homoserine lactone and
   sodium bicarbonate;
and further wherein the culture medium is protein free.

2. The culture medium of claim 1, wherein the pH of the medium is between about pH 5.5 and pH 7.

3. The culture medium of claim 2, wherein the pH of the medium is between about pH 6 and pH 6.8.

4. The culture medium of claim 1, wherein the culture medium further comprises, simple sugars, lipids, and minerals to support the growth of the fastidious microorganism.

5. The culture medium of claim 1, wherein the culture medium comprises cobalt and molybdenum.

6. The culture medium of claim 1, wherein the culture medium does not contain simple sugars.

7. The culture medium of claim 1, wherein the culture medium comprises sucrose, maltose and glucose.

8. The culture medium of claim 1, wherein the culture medium comprises lipids.

9. The culture medium of claim 8, wherein the culture medium comprises lipids that are found in mammalian brain tissue.

10. The culture medium of claim 1, wherein the culture medium comprises NAD and NADP.

11. The culture medium of claim 1, wherein the culture medium comprises sufficient anti-oxidants and reducing agents to support the growth of a fastidious microorganism.

12. A method of culturing a fastidious microorganism comprising culturing a sample containing a fastidious microorganism in a culture medium according to claim 1 for a time and under conditions sufficient to grow a fastidious microorganism present in the sample.

13. The method of claim 12, wherein the fastidious microorganism is a cell wall deficient microorganism.

14. The method of claim 12, wherein the fastidious microorganism is a stressed microorganism.

15. The method of claim 12, wherein the fastidious microorganism is an immunologically impaired microorganism.

16. The method of claim 12, wherein the fastidious microorganism has metabolic defects.

17. The method of claim 12, wherein the fastidious microorganism has defects in nutrient transport.

18. The method of claim 12, wherein the fastidious microorganism is a viable but nonculturable microorganism.

19. The method of claim 12, wherein the culture medium further comprises, simple sugars, lipids, and minerals to support the growth of the fastidious microorganism.

20. The method of claim 12, further comprising passing the sample through one or more filters prior to culturing the sample in the culture medium.

21. The method of claim 12, wherein the sample is cultured in the culture medium for a period of 24 to 72 hours.

22. The method of claim 12, wherein the sample is cultured in the culture medium for a period of two to four weeks.

23. The method of claim 12, wherein the fastidious microorganism is an insect-borne or arachnid-borne microorganism.

24. The method of claim 12, wherein the fastidious microorganism is a mammalian pathogen.

25. The method of claim 24, wherein the mammalian pathogen is pathogenic in a mammal selected from the group consisting of canines, felines, bovines, caprines, equines, ovines, porcines, rodents, lagomorphs, and primates.

26. The method of claim 24, wherein the mammalian pathogen is associated with a condition selected from the group consisting of chronic fatigue syndrome, cancer, hypertension, heart disease, cystic fibrosis, cat scratch disease, renal disease, liver disease, prostate disease, central nervous system disorders, urologic disorders, hyperadrenalcorticism, mastitis, polyarthritis, immune-mediated hemolytic anemia and thrombocytopenia.

27. The method of claim 12, wherein the sample is a biological sample from a mammalian subject.

28. The method of claim 27, wherein the biological sample is a body fluid sample.

29. The method of claim 28, wherein the body fluid sample is selected from the group consisting of blood, plasma, serum, urine, cerebrospinal fluid, pleural fluid, pulmonary mucus, sputum, transudates, modified transudates, exudates, chest fluid, abdominal fluid, synovial fluid, peritoneal fluid, lymph, and effusions.

30. The method of claim 12, wherein the sample is an insect or arachnid sample.

31. The method of claim 12, wherein the sample is a blood product sample.

32. The method of claim 12, wherein the culture medium is a liquid culture medium.

33. The method of claim 12, wherein the culture medium is a solid medium.

34. The method of claim 12, wherein the fastidious microorganism is a bacterium.

35. The method of claim 34, wherein the bacterium is a *Proteobacterium*.

36. The method of claim 34, wherein the bacterium is selected from the group consisting of *Bartonella, Rasbo bacterium, Burcella, Afipa, Burkholdrea pickettli, Streptococcus thermophillis*, and *Corynebacterium*.

37. The method of claim 34, wherein the bacterium is a nanobacterium.

38. The method of claim 34, wherein the bacterium does not have a cell wall.

39. A method of detecting a fastidious microorganism in a sample comprising:
   culturing a sample containing a fastidious microorganism in a culture medium according to claim 1 for a time and under conditions sufficient to grow the fastidious microorganism; and
   detecting the fastidious microorganism.

40. A method of identifying a fastidious microorganism in a sample, comprising:
   culturing a sample containing a fastidious microorganism in a culture medium according to claim 1 for a time and under conditions sufficient to grow the fastidious microorganism; and
   identifying the fastidious microorganism.

41. A method of identifying a compound that binds to a fastidious microorganism, comprising:
   culturing a sample containing a fastidious microorganism in a culture medium according to claim 1 for a time and under conditions sufficient to grow the fastidious microorganism;
   contacting the fastidious microorganism with a compound; and
   detecting binding between the fastidious microorganism and the compound.

42. The method of claim 41, wherein the compound is an antibody.

43. The method of claim 41, wherein the compound reduces the growth or viability of the fastidious microorganism.

44. A method of diagnosing a mammalian subject with an infection by a fastidious microorganism, comprising:
   culturing a sample from a mammalian subject containing a fastidious microorganism in a culture medium according to claim 1 for a time and under conditions sufficient to grow the fastidious microorganism;
   identifying the fastidious microorganism in the cultured sample; and
   diagnosing the subject as having an infection with the fastidious microorganism.

45. A method of diagnosing a disorder in a subject comprising:
   culturing a sample containing a fastidious microorganism in a from a subject culture medium according to claim 1 for a time and under conditions sufficient to grow the fastidious microorganism; and
   identifying the fastidious microorganism in the cultured sample; wherein the presence of the fastidious microorganism in the sample is associated with the disorder.

46. A method of culturing a nanobacterium comprising culturing a sample comprising the nanobacterium in a culture medium according to claim 1 for a time and under conditions sufficient to grow the nanobacterium.

47. A method of culturing *Corynebacteria*, comprising culturing a sample containing *Corynebacteria* in a culture medium according to claim 1 for a time and under conditions sufficient to grow *Corynebacteria* present in the sample.

* * * * *

UNITED STATES PATENT AND TRADEMARK OFFICE
CERTIFICATE OF CORRECTION

PATENT NO. : 7,115,385 B2
APPLICATION NO. : 10/208352
DATED : October 3, 2006
INVENTOR(S) : Breitschwerdt et al.

It is certified that error appears in the above-identified patent and that said Letters Patent is hereby corrected as shown below:

Column 27,
Line 50 should read -- medium further comprises simple sugars, lipids and min- --

Column 28,
Line 31 should read -- further comprises simple sugars, lipids and minerals to --

Column 29,
Line 15 should read -- *bacterium, Burcella, Afipa, Burkholdrea pickettii, Strepto-* --

Column 30,
Line 24 should read -- from a subject in a culture medium according to claim --

Signed and Sealed this

Sixth Day of March, 2007

JON W. DUDAS
*Director of the United States Patent and Trademark Office*